US006033683A

United States Patent [19]
Note-Simonnard et al.

[11] Patent Number: 6,033,683
[45] Date of Patent: Mar. 7, 2000

[54] METHOD OF THE MANUFACTURE OF SUPPOSITORIES

[75] Inventors: Axelle Note-Simonnard; Alain Sirito, both of Monaco, Monaco

[73] Assignee: Techni-Pharma, Monaco

[21] Appl. No.: 08/666,543

[22] PCT Filed: Oct. 5, 1995

[86] PCT No.: PCT/FR95/01294

§ 371 Date: Oct. 21, 1996

§ 102(e) Date: Oct. 21, 1996

[87] PCT Pub. No.: WO96/10987

PCT Pub. Date: Apr. 18, 1996

[30] Foreign Application Priority Data

Oct. 5, 1994 [FR] France ................................. 94 11913

[51] Int. Cl.⁷ .................................................. A61F 9/02
[52] U.S. Cl. ............................................. 424/436; 424/44
[58] Field of Search ................................ 424/1.29–1.33, 424/404, 408, 409, 417, 449, 464, 465, 466, 43, 436, 44

[56] References Cited

U.S. PATENT DOCUMENTS 3,764,668 10/1973 Higuchi et al. .......................... 424/44
5,547,976 8/1996 Slater et al. ............................. 514/410

FOREIGN PATENT DOCUMENTS 0088394  9/1983  European Pat. Off. .
0254693  1/1988  European Pat. Off. .
55-136215  10/1980  Japan .
56-083417  7/1981  Japan .

OTHER PUBLICATIONS

Ijima et al. "Effects of Aerosil 200 and Soybean Lecithin on Release of Carbon Dioxide from Effervescent Suppositories". Yakuzaigaku, vol. 53, No. 1, pp 55–62, 1993.

Hakata et al. "Effects of Bases and Additives on Release of Carbon Dioxide from Effervescent Suppositories". Chem. Pharm. Bull., vol. 41, No. 2, pp 351–356, 1993.

*Primary Examiner*—Donna C. Wortman
*Attorney, Agent, or Firm*—Bierman, Muserlian and Lucas

[57] ABSTRACT

Its subject is more specifically a process for making suppositories releasing carbon dioxide and endowed with a laxative action in which the fatty substances are melted separately and vegetable lecithin is added into the fluid mass resulting from the melting and then a mineral opacifying agent is incorporated, followed by the pouring of potassium acid tartrate and sodium bicarbonate accompanied by stirring, these two constituents having a particular granulometry, and stirring is then continued until perfect homogeneity is achieved before proceeding with the drawing-off of the fluid suspension.

8 Claims, No Drawings

METHOD OF THE MANUFACTURE OF SUPPOSITORIES

The present invention relates to the field of pharmacotechnology.

Its subject is more especially a new process for the preparation of suppositories and in particular of suppositories having a laxative action.

Specifically, its subject is a process for the preparation of suppositories having a laxative action which are capable of causing a release of carbon dioxide by chemical reaction of active principles upon contact with the moisture present in the rectal ampul.

A process is known from French patent n° 788.198 (Waldenmeyer J. G) which offers the possibility of releasing carbon dioxide in the nascent state under the action of moisture or other cause and in which the raw materials releasing this add by their mixture are coated one by one in a fatty substance which protects them against a premature decomposition and which does however allow them to be reached at the moment of use by the catalytic action of a hydrophilic agent.

It may be deduced, on reading this patent, that this could be a process for the preparation of suppositories releasing carbon dioxide, but nothing is said on this subject and only the use of a fatty substance such as cocoa butter can suggest such a use.

A medicinal preparation using this process subsequently appeared on the market. It is formed of a suppository containing an effervescent mixture of potassium acid tartrate and sodium bicarbonate capable, in a moist environment, of releasing ca. 50 ml to 100 ml of carbon dioxide in the rectum.

The problem created by the development of this medicinal preparation lies in the difficulty of realizing a product which does not react prematurely during production or shortly after production, while keeping the desired effervescence properties intact.

One thus finds oneself confronted with a double problem. The active principles are in fact separated from one another by a particularly lipophilic, absolutely tight barrier. Because of the latter, the medicinal preparation is capable of keeping perfectly, but on the other hand the active principles will not be able to react with one another, with the result that such a medicinal preparation is practically inactive.

On the other hand, if the active principles are not coated in an impermeable matrix, they are capable of reacting prematurely amongst themselves in the presentation pack and, above all, they are capable of reacting too violently amongst themselves in the rectal ampul and triggering distensions of the rectal ampul which are too great.

It was thus important to find a coating sufficiently insulating to prevent the constituents of the effervescent mixture from reacting with one another too soon, but also capable of leading, upon contact with a more or less moist mucous membrane, such as the rectal ampul, to a regular, constant and progressive release of carbon dioxide.

This object can be considered to be achieved by the process according to the invention.

In this process, the fatty substances are melted separately, the mixture is left to cool to the desired temperature and vegetable lecithin is dispersed in the fluid mass resulting from the melting, then a mineral opacifying agent is incorporated, and this is followed by the pouring in succession of the potassium acid tartrate, accompanied by stirring, and then of the sodium bicarbonate, accompanied by more vigorous stirring, these two constituents having a particular granulometry, and stirring is then continued until perfect homogeneity is achieved before proceeding with the drawing-off of the fluid suspension into the alveoli of suppositories.

After cooling, suppositories of a regular truncated-cone shape are obtained whose composition is homogeneous and whose preservation, attested by the volume of the release of carbon dioxide, is assured for at least two years.

It is thus clearly seen that the technical problem to be solved is markedly different from that considered by the Waldenmeyer process. At that time, the fatty substances constituted a tight coating which protected completely, and even too completely, against the catalytic action of a hydrophilic agent and it was necessary to incorporate in it a product facilitating the passage of aqueous media.

In contrast, in the present technique, the excipients for suppositories are made from stearates of polyethylene glycol or triglycerides of fatty acids having a medium chain which are substances that are lipophilic and hydrophilic at one and the same time, so that it is necessary to protect the reactive substances of the mixture by an inert protective screen and no longer by lipoid substances.

In a preferred embodiment of the process according to the invention, the fatty substances which act as a support for the realization of suppositories are triglycerides of fatty acids having a medium chain sold under the name Novata BD by the HENKEL company. Those sold under the name Estaram H15 by the UNICHEMA company or those sold under the name Suppocire AM by the GATTEFOSSE company, or those sold under the name Witepsol H 15 by the HÜLS company, can also be used. These triglycerides have a melting range from 35 to 39° C.

Vegetable lecithin is a soya lecithin and in particular the type sold under the name Topcithin 50 by the LUCAS MEYER company or that sold under the name MC Thin AF1 by the same company. Lecithin makes it possible to avoid or reduce thickening of the mass before pouring and is used in the cases of solid active principles which partially solubilize or, above all, in the cases of powdery active principles. Depending on the circumstances, lecithin dissolves in the fatty substance or, on the contrary, remains in suspension.

The opacifying agent is a natural or artificial silicate such as talc or magnesium silicate, or an alkaline-earth metal stearate such as calcium stearate or magnesium stearate, or a derivative of titanium such as titanium dioxide, or a derivative of barium such as barium titanate.

The granulometry of the constituents of the effervescent mixture (potassium acid tartrate and sodium bicarbonate) is adjusted in such a way that the powders have a great fineness and are distributed in a perfectly homogeneous manner without setting under stirring as the preparation proceeds.

The temperature of the suppositories, after pouring into the alveoli, is progressively reduced by cooling until complete solidification.

The thus-realized suppositories have a shelf life of two years, which guarantees their perservation for at least an equal period.

The following example illustrates the invention without, however, limiting it.

EXAMPLE 1

Preparation of effervescent suppositories 36.7 kg of solid hemi-synthetic glycerides are introduced into a stainless steel tank and melted at a temperature between 35 and 39° C. 4.2 kg of soya lecithin are then added, accompanied by stirring. 2.1 kg of talc are then progressively incorporated, still accompanied by stirring. After the homogeneity of the suspension has been realized, 23 kg of potassium acid tartrate are added in small portions and accompanied by vigorous stirring and then 14 kg of sodium bicarbonate.

The ingredients are left to mix for 10 minutes and then, while maintaining the temperature, the suspension is taken off and the alveoli are thus filled and passed into a cooling enclosure until solidification is complete.

Determination of the effervescence of the suppositories:

Principle

Monitoring of effervescence by measuring the release of carbon dioxide at 37° C.

Technique

The suppository is quickly introduced into a test-tube A (100 ml) filled with water at 37° C. and the latter is closed with a fritted glass stopper (porosity 2) fitted with a rubber joint, while ensuring that no air bubbles are trapped.

The test-tube A is immersed in a second test-tube B (250 ml) filled with water at 37° C. and containing a magnetic bar. Test-tube B is placed in a water bath at ca. 40° C., arranged on a heating magnetic stirrer, so as to maintain a constant temperature (37°±1° C.).

The magnetic stirring and the heating are maintained throughout the gaseous release. The volume of carbon dioxide is read off from test-piece A.

Tests of the stability of the effervescent suppositories and measurement of the effervescent suppositories and measurement of the released carbon dioxide.

The effervescence checks were carried out on several production batches realized at three different times.

These checks were carried out:

on a single blister from the start, from the middle or from the end of production and on several blisters from the start, from the middle and from the end of production.

These checks made it possible to demonstrate:

on a single blister taken at a given moment during production (start, middle or end), the maximum difference in the volume of carbon dioxide released and thus the intra-blister homogeneity;

on several blisters taken at different moments during production (start, middle or end), the maximum difference in the volume of carbon dioxide released and thus the inter-blister homogeneity;

the average volume of carbon dioxide released at the start, in the middle and at the end of production;

the average global volume of released carbon dioxide.

All these checks were carried out in a 250 ml test-tube.

The conclusions are as follows:

The average gaseous release is between 50 and 100 ml.

There is no significant reduction in the volume of released carbon dioxide between a batch at time 0 and a batch prepared two years previously. The best gaseous release are found, in the majority of cases, in the middle of production and the worst releases are found, in the majority of cases, at the end of production. To be more specific, the checks carried out produced the following results:

| Production | Start | 10 hours | 12 hours | 14 hours | End |
|---|---|---|---|---|---|
| Effervescence | Batch 1 | Batch 2 | Batch 3 | Batch 4 | Batch 5 |
| Check n° 1 | 94 ml | 80 ml | 80 ml | 76 ml | 76 ml |
| Check n° 2 | 91 ml | 84 ml | 86 ml | 82 ml | 80 ml |
| Check n° 3 | 93 ml | 73 ml | 84 ml | 80 ml | 78 ml |

In conclusion, the variations recorded take account at one and the same time of the difficulty of obtaining an absolutely homogeneous preparation and also the uncertain sensitivity of the methods of assessing the volume of gaseous release because of the solubility of carbon dioxide in water.

What is claimed is:

1. A process for the preparation of homogeneous suppositories causing a constant release of carbon dioxide by chemical reaction of reactive mixture upon contact with moisture, comprising separately melting the excipient of the suppository, incorporating about 5% by weight of vegetable lecithin into the mixture, followed by admixture of about 2.5% by weight of a mineral opacifying agent, and then while stirring adding the elements that generate carbon dioxide until the mixture becomes perfectly and permanently homogeneous, pouring the mixture into plastic molds and drawing off the fluid suspension into the suppository mold alveoli held in a cooling device until solidification occurs, to prepare shelf stable effervescent suppositories.

2. The process for the preparation of suppositories of claim 1 wherein the excipient is a fatty substance which melts between 35 and 39° C. and in which a monopotassium salt of a difunctional acid and an alkaline bicarbonate are incorporated as elements which generate carbon dioxide.

3. The process according to claim 1 wherein the monopotassium salt of a difunctional acid which is a potassium acid tartrate, then an alkali metal bicarbonate, are successively added to the excipient of the suppository, the two constituents having a specific granulometry.

4. The process for the preparation of suppositories of claim 1 wherein the fatty substances are stearates of polyethylene glycol or triglycerides of fatty acids having lipophilic and hydrophilic properties.

5. The process according to claim 1 wherein triglycerides of fatty acid having a medium chain are used as fatty substances.

6. The process according to claim 1 wherein triglycerides of fatty acids having a medium chain that are used as excipients are those which have a melting range from 35 to 39° C.

7. The process according to claim 1 wherein the vegetable lecithin is a soya lecithin.

8. The process according to claim 1 wherein the opacifying agent is selected from the group consisting of a natural or artificial silicate, an alkaline-earth metal stearate, magnesium stearate, titanium dioxide and an insoluble titanate.

* * * * *